United States Patent
Fleissman

(10) Patent No.: US 6,660,277 B1
(45) Date of Patent: Dec. 9, 2003

(54) GEL MATRIX NON-EMULSION COMPOSITION CONTAINING TWO CLAY GELS

(75) Inventor: Leona Giat Fleissman, Ridgewood, NJ (US)

(73) Assignee: Avon Products, Inc., Suffern, NY (US)

( * ) Notice: Subject to any disclaimer, the term of this patent is extended or adjusted under 35 U.S.C. 154(b) by 0 days.

(21) Appl. No.: 09/100,835

(22) Filed: Jun. 19, 1998

(51) Int. Cl.[7] .............. A61K 7/48; A61K 9/10; A61K 33/08; A61K 47/02
(52) U.S. Cl. .............. 424/400; 424/484; 424/684; 514/937; 514/770; 514/844; 514/847; 516/34; 516/79; 516/110; 516/903; 516/923
(58) Field of Search .................. 424/484, 400, 424/684; 514/937, 938, 844, 847, 770; 516/34, 79, 110, 903, 923

(56) References Cited

U.S. PATENT DOCUMENTS

| | | |
|---|---|---|
| 2,409,338 A | 10/1946 | Alton et al. |
| 3,429,826 A | 2/1969 | Alburger |
| 3,920,883 A | 11/1975 | Yamada et al. |
| 4,087,555 A | 5/1978 | Barnett et al. |
| 4,116,866 A * | 9/1978 | Finlayson |
| 4,237,112 A | 12/1980 | Selega et al. |
| 4,379,755 A | 4/1983 | Yamada et al. |
| 4,446,051 A | 5/1984 | Berthod et al. |
| 4,467,081 A | 8/1984 | Chang et al. |
| 4,637,933 A | 1/1987 | Zabotto nee Arribau et al. |
| 4,701,318 A * | 10/1987 | Ferlauto, Jr. et al. |
| 4,707,293 A | 11/1987 | Ferro |
| 4,717,735 A | 1/1988 | Strem |
| 4,874,605 A | 10/1989 | Urban, Jr. et al. |
| 4,929,644 A | 5/1990 | Guilbeaux |
| 4,985,250 A | 1/1991 | Bee et al. |
| 5,002,974 A | 3/1991 | Geria |
| 5,015,469 A | 5/1991 | Yoneyama et al. |
| 5,139,782 A | 8/1992 | Jung |
| 5,215,759 A | 6/1993 | Mausner |
| 5,258,184 A | 11/1993 | Bee et al. |
| 5,478,561 A | 12/1995 | Ferrero |
| 5,532,000 A | 7/1996 | Kauffmann |
| 5,538,728 A | 7/1996 | Yanaki et al. |
| 5,569,465 A | 10/1996 | Kauffmann |
| 5,626,853 A | 5/1997 | Bara et al. |
| 5,656,289 A | 8/1997 | Cho et al. |
| 5,658,575 A | 8/1997 | Ribier et al. |
| 5,674,504 A | 10/1997 | Kauffmann |
| 5,674,508 A | 10/1997 | Deserable et al. |
| 5,702,709 A * | 12/1997 | Schulz et al. |
| 5,869,033 A * | 2/1999 | Schulz |

FOREIGN PATENT DOCUMENTS

| | | |
|---|---|---|
| DE | 2910473 | 9/1979 |
| GB | 2021411 | 12/1979 |

* cited by examiner

*Primary Examiner*—Edward J. Webman
(74) *Attorney, Agent, or Firm*—Ohlandt, Greeley, Ruggiero & Perle LLP

(57) ABSTRACT

A cosmetic composition comprising a lipophilic clay gel and a hydrophilic clay gel. The two gels are combined or formed in situ to create a gel matrix. This matrix functions like an emulsion to deliver water and oil to the skin or other surface, but can be substantially free of surfactants, emulsifiers and waxes. A method for the preparation of a clay gel matrix is also revealed.

12 Claims, No Drawings

GEL MATRIX NON-EMULSION COMPOSITION CONTAINING TWO CLAY GELS

The present invention relates generally to non-emulsion cosmetic compositions containing clay gels. More particularly, this invention relates to a cosmetic composition having two clay gels. The two gels are an organophilic, lipophilic clay gelled with a polar solvent and a hydrophilic clay gelled with water. The two gels are combined. The resulting composition or gel matrix is used as a base for cosmetic compositions. This gel matrix is a substitute for traditional emulsion-based systems.

BACKGROUND OF THE INVENTION

Various cosmetic bases are known for use in cosmetic compositions, such as liquids, creams, gels and lotions. Traditionally, these cosmetic bases are formed as emulsions (e.g., water-in-oil, oil-in-water, triple emulsions, microemulsions) to permit the delivery of water and oils to the skin, hair, nails or other surface to be treated. However, many consumers find that the emulsifiers and surfactants typically used to form these emulsions are drying or irritating to the skin. Furthermore, the manufacture of emulsions frequently requires the application of high shear to the oil/water mixture, thus prolonging and increasing the expense of the manufacturing process. Accordingly, a demand exists for cosmetic base compositions that are substantially free from emulsifiers and surfactants.

Clay-based gels are known in the art. Many clays, such as smectite clays, are known to form gels in water. Modified clays have been developed that are organophilic, and consequently form gels in organic solvents. A preferred subset of these modified clays are lipophilic. In this regard, reference is made to copending U.S. patent application Ser. No. 08/853,992, which is commonly owned by the assignee of the present application, and which is incorporated herein by reference. This application discloses a superior gel product formed from such organically modified clays and polar organic solvent oils. However, the prior art has recognized and considered the hydrophilic clay gels as separate from, alternative to, and presumably incompatible with the lipophilic clay gels.

Accordingly, there is a need for a cosmetic composition that can be used as a cosmetic base and carrier for cosmetic ingredients such as pigments, preservatives, moisturizers, humectants, fragrances, healing and treatment agents, and that is substantially free of emulsifiers and surfactants and, perhaps, non-clay stabilizers and thickeners.

SUMMARY OF THE INVENTION

Against the foregoing background, it is a primary object of the present invention to provide a cosmetic composition that has a significantly lower concentration of emulsifiers and surfactants than traditional cosmetic compositions.

It is another object of the present invention to provide a cosmetic composition having a gelled carrier that is substantially free of emulsifiers and surfactants.

It is a further object of the present invention to provide a cosmetic composition that can be formulated at low temperature and with the application of minimal shear.

It is yet another object of the present invention to provide a cosmetic composition that can be formulated as two separate clay gels that are subsequently combined into a stable composition, or formed together in situ.

It is a further object of the present invention to provide a cosmetic composition that is substantially free from non-clay stabilizers and thickeners.

To the accomplishment of the foregoing objects and advantages, the present invention, in brief summary, is a cosmetic composition comprising a hydrophilic clay gel and a lipophilic clay gel, combined together in a stable gel matrix or lattice. A method for the preparation of a dual clay gel is also provided.

DESCRIPTION OF THE PREFERRED EMBODIMENTS

The present invention provides a unique cosmetic composition (or vehicle) formed from a hydrophilic clay gel and a lipophilic clay gel. Each clay is formed into a gel, as described below. The two gels are combined or formed in situ to form a gel matrix. The gel matrix delivers both water and oil to the skin, without the need for traditional emulsifiers or surfactants. Also, typical stabilizers and thickeners, such as waxes, can also be eliminated entirely, or used in substantially lower amounts.

The preferred two or more clays used in the present invention are, smectite-type clays. Both naturally-occurring and synthetic clays are suitable for use. However, synthetic clays are preferred for their consistency and relative freedom from impurities. Nonetheless, any naturally-occurring clay that has been cleaned to remove impurities is highly suitable for use in the present invention.

A most preferred hydrophilic clay for use in the present invention includes Lucentite SWN. Lucentite SWN is a lithium magnesium sodium silicate. This synthetic silicate clay of the miontmorillonite group is substantially the same as the Lucentite SAN discussed below, but has no quaternium-18 added thereto. This clay is preferred for its swelling capacity under low shear and its compatibility with Lucentite SAN. Additionally, because it is synthetically synthesized, it is more efficient due to its lack of contaminants. Closely related water swellable clays, such as other montmorillonite-type clays, are also preferred for use as the hydrophilic clay or clays of the present invention.

The hydrophilic (or water-swellable) clay or clays (one clay or a combination of clays can be used) are gelled (e.g., prior to combination with the organic phase, in combination with the organic phase, or in stages) by methods known in the art. It is preferred that the hydrophilic clay is gelled in demineralized water. However, other types of water, as well as aqueous solutions, can be used to form the gel with the hydrophilic clay or clays.

The hydrophilic or water-based gel (in a basic two clay, two solvent, nonpigmented system) is preferably about 2 weight percent to about 15 weight percent clay, and about 98 weight percent to about 85 weight percent water. More preferably, this gel is about 3 weight percent to about 6 weight percent clay, and about 97 weight percent to about 94 weight percent water. Optimally, about 4 weight percent clay and about 96 weight percent water are used. The addition of pigments or other powders (or other cosmetic additives) to the system will influence the optimal amount of clay to be used. As pigment or other ingredients are added, the preferred relative proportion of the clay and solvent components will be adjusted accordingly.

The lipophilic (or oil-swellable) clay is also formed with a solvent into a clay gel (e.g., prior to combination with the water-based phase, in combination with the water-based phase, or in stages). A most preferred lipophilic clay or clays (one clay or a combination of clays can be used) for use in the gel matrix of the present invention include the synthetic smectite clay commercially available as Lucentite SAN. This smectite clay is a lithium magnesium sodium silicate that is combined, but not reacted, with quaternium-18. A further discussion of this clay can be found in copending U.S. patent application Ser. No. 08/853,992, incorporated above by reference. Other preferred lipophilic clays include bentonites, laponites and other lipophilic smectite clays.

A discussion of the preferred oil-type solvent or solvents (one solvent or a combination of solvents may be employed) used to form a gel with the lipophilic clay or clays is also included in U.S. patent application Ser. No. 08/853,992, discussed above. The smectite clay is preferably gelled with a polar lipophilic organic solvent to provide a lipophilic, organic-based clay gel.

The most preferred polar lipophilic organic solvents are benzoate esters, such as $C_{12-15}$ alcohols benzoate (Finsolv TN), and salicylate esters. However, the solvent $C_{12-15}$ alcohol lactate is also preferred, since it also swells the synthetic smectite effectively. Silicones can also be used as the preferred solvents. Other preferred oil-type solvents include $C_{12}$–$C_{15}$ alcohol lactate (Ceraphyl 41 from ISP) and $C_{12}$–$C_{15}$ alcohol octanoate. Still other preferred solvents include phenyl trimethicone, Finsolv SB, Finsolv BOD, Finsolv PG-22, Surfadone LP300, Finsolv 116, Finsolv 137, Finsolv EMG20, alkyl 12–15 salicylate, tridecyl salicylate, isocetyl salicylate, laureth 2-benzoate, and phenylethylmethyl polydimethylsiloxane. Any aliphatic or aromatic polar solvent, organosilicone, ester, or compound or derivative thereof, can be used in the present invention.

As discussed in the related application, in regard to the clear or translucent property of the finished product, the most preferred solvents, benzoate esters, form transparent gels when combined with the smectite clay and swelled with the application of heat. Finsolv TN ($C_{12}$–$C_{15}$ alcohols benzoate) is the most preferred ester for use in the compositions of the present invention. Pure $C_{12}$ and $C_{18}$ alcohols benzoate performed equivalently. When the smectite clay, preferably smectite SAN, is combined with octyl salicylate, a totally clear gel is also formed. However, the gel strength is less than that of the Finsolv TN gel. Guerbet alcohols such as butyl octyl salicylate, butyl octyl benzoate and hexyl decyl benzoate also perform well as solvents.

The lipophilic, organic-based clay gel is preferably about 5 weight percent to about 20 weight percent clay, and about 80 weight percent to about 95 weight percent organic solvent. More preferably, about 5 weight percent to about 15 weight percent clay, and about 85 weight percent to about 95 weight percent organic solvent are used. Optimally, about 10 weight percent clay is used to form the lipophilic clay gel of the present invention. If pigments or other powders (or other cosmetic additives) are added to the formulation, the preferred relative proportion of the clay and solvent components will consequently be adjusted.

It is preferred that the two clay gels be combined in roughly equal proportions, although depending on the results to be achieved by the desired composition, and its desired consistency and feel on application, differing proportions can be used. For example, a higher relative proportion of the lipophilic clay gel may be used to achieve a richer, more emollient formulation. In a non-pigmented formulation, two parts oil phase to one part water phase produces a heavier, richer composition. Alternatively, a higher relative proportion of the water-based clay gel may be used, to achieve a fresher, lighter weight formulation. For example, in a non-pigmented formulation, two parts water-based to one part oil-based clay gel produces a gel matrix that results in a lighter creme-type composition. Up to about 20 parts water to one part oil can preferably be used in the gel matrices of the present invention. On the other end of the spectrum, up to about 20 parts oil to one part water can preferably be used in the gel matrices of the present invention.

Furthermore, while an even distribution and mixture of the two clay gels is generally preferred, it may be desirable to inject or otherwise place one of the gels in one or more pockets or layers of higher concentration within or upon the other gel. This arrangement can be used to achieve unique visual or textural aesthetic effects. The gels can subsequently be further integrated by the end user, or can be applied as provided.

The viscosity of the gel matrix can be modified to achieve the desired consistency by methods known in the art. For example, by increasing the proportion of the clays in the individual gels, a thicker, more viscous product is achieved. This cream-type product is more easily retained in the precise location on which it is applied on the skin or other surface. By increasing the proportion of the solvents (water and the organic solvent) in the respective gels, a thinner, less viscous product is produced. This lotion-type product is more easily applied to and spread over the skin. In addition, the gels can form a solid or semi-solid that can be applied like a cake-type product. Moreover, non-clay viscosity modifiers can also be used to adjust the consistency of the gel matrix formulations (e.g. pigments and other powders, such as nylon sphericals and silicon dioxide). These modifiers are preferably added to one or both of the individual clay/solvent mixtures prior to gelling, but can also be incorporated into the combined gel matrix.

The resulting gel matrix can be used as a moisturizing composition for application to the skin, nails, hair or other surface. In a more typical application, however, the gel matrix is used as a cosmetic base, suitable for delivery of colorants, treatment agents, sunscreens, healing agents or other additives evenly dispersed throughout the gel matrix to the skin.

Without desiring to be bound by theory, it is believed that the similarity in composition and three-dimensional structure of the preferred Lucentite SWN and of Lucentite SAN, the preferred oil swellable clay, facilitates formation of the stable gel matrix lattice of the present invention, minimizes the added energy needed to form the lattice, and increases the stability of the lattice.

A preferred gel matrix-based cosmetic according to the present invention is set forth below in two embodiments. One embodiment is a concealer, having conventional cosmetic pigments therein. The other embodiment is a vehicle or non-pigmented moisturizing composition.

Concealer (With Powder)/Moisturizer

|  | Weight Percent | |
| --- | --- | --- |
| Ingredient | With Powders | No Powders |
| Oil Phase | | |
| Smectite SAN (Lucentite) | 3.08 | 3.33 |
| Finsolv TN | 27.69 | 30.00 |

-continued

| Ingredient | Weight Percent | |
| --- | --- | --- |
| | With Powders | No Powders |
| Water Phase | | |
| Smectite SWN (Lucentite) | 2.46 | 2.67 |
| Deionized water | 59.08 | 64.00 |
| Powder Phase | | |
| Conventional cosmetic powders | 7.69 | 0 |

Both of the foregoing compositions are preferably formulated by mixing the phases cold (at room temperature). The oil phase is then added to the water phase, again under cold conditions. The optional powder phase is then added to the mixture. The resulting mixture has a thin consistency, and is optionally allowed to stand for several hours or overnight. The mixture develops a thicker consistency after standing. It is then heated with mixing in a hot water bath. The resulting stable gel matrix that is formed shows no phase separation, syneresis or other breakdown.

It is believed preferable to add the optional powder phase after the oil phase and water phase are gelled. However, the optional powder phase may be added to either or a combination of the oil and water phases prior to their formation into a gel.

Because the gel matrices of the present invention are gels and do not need waxes, each gel or phase itself can be formulated to be clear or translucent. When mixed, the preferred inter-reacted gels tend to become opaque. Although opaque, the lack of waxes enables the gel matrix to achieve true color presentation. This provides a greater ability to produce an aesthetically unique and appealing product due to the clearer, truer colors of the gel matrix of the present invention. Furthermore, the finished product has good payoff and/or spreadability, a smooth and creamy feel on application, and even delivery to the skin.

Compositions using the gel matrices of the present invention are also beneficial because they have superior high temperature stability. For example, they will not melt or disassociate readily in hot climates or in hot car trunks. Furthermore, these compositions can be formulated to be wax free, and are resistant to or free of syneresis. The gel matrix compositions show no creaming and no separation, unlike prior art clay mixtures. They have excellent suspension properties, and are not salt sensitive (unlike Carbopols). Accordingly, they achieve the objectives of emulsions, without the drawbacks associated with emulsions and emulsifiers.

As exemplified above, the dual gel matrix compositions of the present invention are preferably formed by the following method: The hydrophilic clay is mixed with water and the lipophilic clay is separately mixed with the oil or oils. Both mixtures are made at room temperature, with low shear, and the mixtures are allowed to stabilize. The two mixtures are subsequently combined, and this resulting mixture is then heated and allowed to gel and set. A stable, sturdy gel matrix results. Accordingly, the preferred gel matrix is formed in situ. It has been found that it is easiest to form the gel matrix of the present invention by swelling the lipophilic clay after it is combined with a partially swelled hydrophilic gel. Further gelling of the hydrophilic gel can occur in conjunction with the swelling of the lipophilic clay.

Alternatively the gels can be formed separately and set, and subsequently combined by simple mixing under low shear and at room temperature. The subsequent application of heat or high shear to the system can provide further stability to the resulting mixture. Other methods can be used to combine the gel phases, and are within the contemplation of the present invention.

More specifically, a preferred composition according to the present invention is formulated by the following steps:
1) mixing with minimal shear the synthetic lipophilic clay and the polar solvent at ambient to cold temperatures;
2) mixing with minimal shear the hydrophilic clay and water at ambient temperature;
3) allowing the water-based mixture to gel;
4) adding the polar solvent-based dispersion into the water-based gel; and
5) applying heat to the mixture of step 4) to swell and set the gel formed therein.

Alternatively, as discussed above, the lipophilic clay gel can be heat set and swelled prior to its combination with the water-based gel. It has also been found that a stable gel matrix can be formed by combining the hydrophilic clay powder with the lipophilic clay powder, separately combining the water to be gelled with the oil to be gelled, and finally mixing the clay powders with the liquids. The gel matrix formed in situ in this manner is also stable and has good aesthetic properties.

While an advantage of the gel matrices of the present invention is their ability to deliver oils, water and other cosmetic ingredients to the skin substantially without the use of surfactants, it is possible to add surfactants to these gel matrices. Such surfactants are not used to emulsify, but can be used for their foaming properties, to incorporate an emulsified film-former, or for other functions.

The gel matrices of the present invention can be enhanced with cosmetic active ingredients, such as skin treatment agents, colorants, feel modifiers, bioactive molecules, wound healing agents (for which a gentle, substantially surfactant-free vehicle is particularly beneficial), and hypoallergenic products.

While the primary utility of the gel matrices is seen to be cosmetic vehicles and compositions, it is also envisioned that the gel matrices would be useful in such disparate fields as the clean-up of solvent spills (by gelling and isolating the solvent), or the use of food grade clays in edible products formed with dual gel matrices of the present invention.

When the gel matrices of the present invention are compared to traditional emulsions, several points of distinction become evident. First, it is known that an emulsion will readily disperse in its external phase. For example, an oil-in-water emulsion, having a water external phase, will readily disperse if dispensed into a container of water. However, the gel matrices of the present invention do not disperse in water or in oil.

In light of the foregoing, the gel matrices of the present invention are not believed to be structured with a conventional external phase and internal phase, like an oil-in-water emulsion that has an aqueous continuous phase to conduct electrical current. Yet, it has surprisingly been found that they do conduct electrical current like such an emulsion. This is further support for the conclusion that the gel matrices have a unique structure, one which is capable of conducting electricity without having a conventional continuous phase. This surprising result should indicate that an emulsifier would not be needed to disperse the gel matrix in water. However, as discussed above, such an unassisted dispersion does not occur in water.

Furthermore, a typical emulsion will break if salt is added to it, because of its sensitivity to electrolytes. However, representative gel matrices of the present invention; when mixed in equal proportions with salt, do not lose their gel integrity. Even at this very high salt concentration, the gel matrices of the present invention continue to possess structure, and do not show the salt sensitivity of an emulsion.

In addition, particle size analysis shows a marked difference between typical emulsion particle size and the particle size of the gel matrices of the present invention. The mean particle size of a gel matrix according to the present invention has been found to be significantly larger than that of a typical emulsion.

The present invention having been thus described with particular reference to the preferred forms thereof, it will be obvious that various changes and modifications may be made therein without departing from the spirit and scope of the invention as defined in the appended claims.

I claim:

1. A cosmetic composition comprising:
    a hydrophilic clay gel containing a hydrophilic clay and water; and
    a lipophilic clay gel containing a lipophilic clay and an organic solvent,
    wherein said hydrophilic clay gel and said lipophilic clay gel form a gel matrix.

2. The cosmetic composition of claim 1, wherein at least one of said clays is synthetic.

3. The cosmetic composition of claim 1, wherein at least one of said lipophilic clay and said hydrophilic clay includes synthetic lithium magnesium sodium silicate.

4. The cosmetic composition of claim 1, wherein both of said lipophilic clay and said hydrophilic clay include synthetic lithium magnesium sodium silicate.

5. The cosmetic composition of claim 1, wherein said lipophilic clay includes lithium magnesium sodium silicate and quaternium-18.

6. The cosmetic composition of claim 1, wherein said hydrophilic clay is present at about 2 to about 15 weight percent of said hydrophilic clay gel.

7. The cosmetic composition of claim 1, wherein said lipophilic clay is present at about 5 to about 20 weight percent of said lipophilic clay gel.

8. The cosmetic composition of claim 1, further comprising a cosmetic active ingredient.

9. The cosmetic composition of claim 1, wherein said cosmetic composition is substantially wax-free.

10. A cosmetic composition comprising:
    a hydrophilic clay gel containing a hydrophilic clay and water; and
    a lipophilic clay gel containing a lipophilic clay and an organic solvent,
    wherein said hydrophilic clay gel and said lipophilic clay gel form a gel matrix, and wherein said composition is substantially free of all emulsifiers, surfactants, and waxes.

11. The cosmetic composition of claim 10, wherein said hydrophilic clay is present at about 2 to about 15 weight percent of said hydrophilic clay gel.

12. The cosmetic composition of claim 10, wherein said lipophilic clay is present at about 5 to about 20 weight percent of said lipophilic clay gel.

* * * * *